(12) United States Patent
Cambronne (10) Patent No.: US 10,052,124 B2
(45) Date of Patent: Aug. 21, 2018

(54) ROTATIONAL ATHERECTOMY DEVICE WITH A SYSTEM OF ECCENTRIC ABRADING HEADS

(71) Applicant: Cardiovascular Systems, Inc., New Brighton, MN (US)

(72) Inventor: Matthew David Cambronne, Mounds View, MN (US)

(73) Assignee: Cardiovascular Systems, Inc., New Brighton, MN (US)

(*) Notice: Subject to any disclaimer, the term of this patent is extended or adjusted under 35 U.S.C. 154(b) by 315 days.

(21) Appl. No.: 15/059,349

(22) Filed: Mar. 3, 2016

(65) Prior Publication Data

US 2016/0183968 A1 Jun. 30, 2016

Related U.S. Application Data

(62) Division of application No. 13/621,398, filed on Sep. 17, 2012, now Pat. No. 9,289,230.

(51) Int. Cl.
*A61B 17/22* (2006.01)
*A61B 17/3207* (2006.01)
*A61M 25/09* (2006.01)
*A61B 17/32* (2006.01)

(52) U.S. Cl.
CPC .. *A61B 17/320758* (2013.01); *A61B 17/3207* (2013.01); *A61B 2017/320004* (2013.01); *A61B 2017/320032* (2013.01); *A61B 2017/320766* (2013.01); *A61M 25/09* (2013.01); *A61M 2025/09083* (2013.01); *A61M 2025/09183* (2013.01)

(58) Field of Classification Search
CPC ............ A61B 17/3202; A61B 17/3207; A61B 17/320758; A61B 2017/320004; A61B 2017/320032; A61B 17/320766; A61M 2025/09183
See application file for complete search history.

(56) References Cited

U.S. PATENT DOCUMENTS

2008/0306498 A1* 12/2008 Thatcher ........ A61B 17/320758
606/159

* cited by examiner

*Primary Examiner* — Robert Lynch
(74) *Attorney, Agent, or Firm* — Barnes & Thornburg LLP; Jeffrey R. Stone (57) ABSTRACT

The invention provides a rotational atherectomy device having a flexible, elongated, rotatable drive shaft with a system of eccentric abrading heads attached thereto. The eccentric enlarged abrading heads may have centers of mass spaced radially from the rotational axis of the drive shaft, wherein adjacent eccentric abrading heads, and centers of mass thereof, are rotationally separated from each other on the drive shaft.

20 Claims, 9 Drawing Sheets

Fig. 10

ROTATIONAL ATHERECTOMY DEVICE WITH A SYSTEM OF ECCENTRIC ABRADING HEADS

CROSS-REFERENCE TO RELATED APPLICATIONS

This is a divisional of patent application Ser. No. 13/621,398 filed Sep. 17, 2012, which is incorporated herein by reference.

BACKGROUND OF THE INVENTION

1. Field of the Invention

The invention relates to devices and methods for removing tissue from body passageways, such as removal of atherosclerotic plaque from arteries, utilizing a high-speed rotational atherectomy device.

2. Description of the Related Art

A variety of techniques and instruments have been developed for use in the removal or repair of tissue in arteries and similar body passageways. A frequent objective of such techniques and instruments is the removal of atherosclerotic plaques in a patient's arteries. Atherosclerosis is characterized by the buildup of fatty deposits (atheromas) in the intimal layer (under the endothelium) of a patient's blood vessels. Very often over time, what initially is deposited as relatively soft, cholesterol-rich atheromatous material hardens into a calcified atherosclerotic plaque. Such atheromas restrict the flow of blood, and therefore often are referred to as stenotic lesions or stenoses, the blocking material being referred to as stenotic material. If left untreated, such stenoses can cause angina, hypertension, myocardial infarction, strokes and the like.

Rotational atherectomy procedures have become a common technique for removing such stenotic material. Such procedures are used most frequently to initiate the opening of calcified lesions in coronary arteries. Most often the rotational atherectomy procedure is not used alone, but is followed by a balloon angioplasty procedure, which, in turn, is very frequently followed by placement of a stent to assist in maintaining patency of the opened artery. For non-calcified lesions, balloon angioplasty most often is used alone to open the artery, and stents often are placed to maintain patency of the opened artery. Studies have shown, however, that a significant percentage of patients who have undergone balloon angioplasty and had a stent placed in an artery experience stent restenosis—i.e., blockage of the stent which most frequently develops over a period of time as a result of excessive growth of scar tissue within the stent. In such situations an atherectomy procedure is the preferred procedure to remove the excessive scar tissue from the stent (balloon angioplasty being not very effective within the stent), thereby restoring the patency of the artery.

Several kinds of rotational atherectomy devices have been developed for attempting to remove stenotic material. In one type of device, such as that shown in U.S. Pat. No. 4,990,134 (Auth), a burr covered with an abrasive abrading material such as diamond particles is carried at the distal end of a flexible drive shaft. The burr is rotated at high speeds (typically, e.g., in the range of about 150,000-190,000 rpm) while it is advanced across the stenosis. As the burr is removing stenotic tissue, however, it blocks blood flow. Once the burr has been advanced across the stenosis, the artery will have been opened to a diameter equal to or only slightly larger than the maximum outer diameter of the burr. Frequently more than one size burr must be utilized to open an artery to the desired diameter.

U.S. Pat. No. 5,314,438 (Shturman) discloses another atherectomy device having a drive shaft with a section of the drive shaft having an enlarged diameter, at least a segment of this enlarged surface being covered with an abrasive material to define an abrasive segment of the drive shaft. When rotated at high speeds, the abrasive segment is capable of removing stenotic tissue from an artery. The disclosure of U.S. Pat. No. 5,314,438 is hereby incorporated by reference in its entirety.

U.S. Pat. No. 5,681,336 (Clement) provides an eccentric tissue removing burr with a coating of abrasive particles secured to a portion of its outer surface by a suitable binding material. This construction is limited, however because, as Clement explains at Col. 3, lines 53-55, that the asymmetrical burr is rotated at "lower speeds than are used with high speed ablation devices, to compensate for heat or imbalance." That is, given both the size and mass of the solid burr, it is infeasible to rotate the burr at the high speeds used during atherectomy procedures, i.e., 20,000-200,000 rpm. Essentially, in this prior art device, the center of mass offset from the rotational axis of the drive shaft would result in development of significant centrifugal force, exerting too much pressure on the wall of the artery and creating too much heat and excessively large particles.

U.S. Pat. No. 5,584,843 (Wulfman) discloses one or more ellipsoidal burrs or cuffs attached to a flexible drive shaft. The drive shaft is placed over a preformed shaped guidewire so that the drive shaft and burrs conform to the shape and profile of the guide wire, i.e., a gentle "S" or "cork-screw" shape. Wulfman, however, requires the preformed guidewire to achieve the non-linear shaping of the drive shaft, a deformed shaping state that is, therefore, present when the device is not rotated. Thus, Wulfman's burrs comprise a sweeping diameter that is limited to, and by, the guidewire shaping. In addition, each of Wulfman's burrs are elliptical and symmetric about the rotational axis of the drive shaft with each center of mass for the burrs being on the drive shaft's rotational axis. Thus, the sweeping diameter of Wulfman is not induced by rotational speed and, therefore, cannot be controlled other than by the guidewire's shaping. Difficulties in positioning the shaped, undeformed, guidewire without damaging the patient's vasculature are also present.

The present invention overcomes these deficiencies.

BRIEF SUMMARY OF THE INVENTION

The invention provides a rotational atherectomy device having, in various embodiments, a flexible, elongated, rotatable drive shaft with a system of eccentric abrading heads attached thereto. At least part of the eccentric enlarged abrading heads in the system have a tissue removing surface—typically an abrasive surface. In certain embodiments, the abrading heads may be at least partially hollow. Preferably the eccentric enlarged abrading heads have centers of mass spaced radially from the rotational axis of the drive shaft, facilitating the ability of the system of eccentric abrading heads to work together to open the stenotic lesion to a diameter substantially larger than the outer resting diameter of the enlarged abrading heads when operated at high speeds. Therefore, certain embodiments comprise a system having unbalanced centers of mass to not only stimulate greater rotational diameters but also arranged in a manner whereby a debris-removing augering effect occurs. Alternatively, other embodiments may comprise systems having abrading heads with balanced centers of mass.

The figures and the detailed description which follow more particularly exemplify these and other embodiments of the invention.

BRIEF DESCRIPTION OF THE DRAWINGS

The invention may be more completely understood in consideration of the following detailed description of various embodiments of the invention in connection with the accompanying drawings, which are as follows.

DETAILED DESCRIPTION OF THE INVENTION, INCLUDING THE BEST MODE

While the invention is amenable to various modifications and alternative forms, specifics thereof are shown by way of example in the drawings and described in detail herein. It should be understood, however, that the intention is not to limit the invention to the particular embodiments described. On the contrary, the intention is to cover all modifications, equivalents, and alternatives falling within the spirit and scope of the invention.

Figure 1:
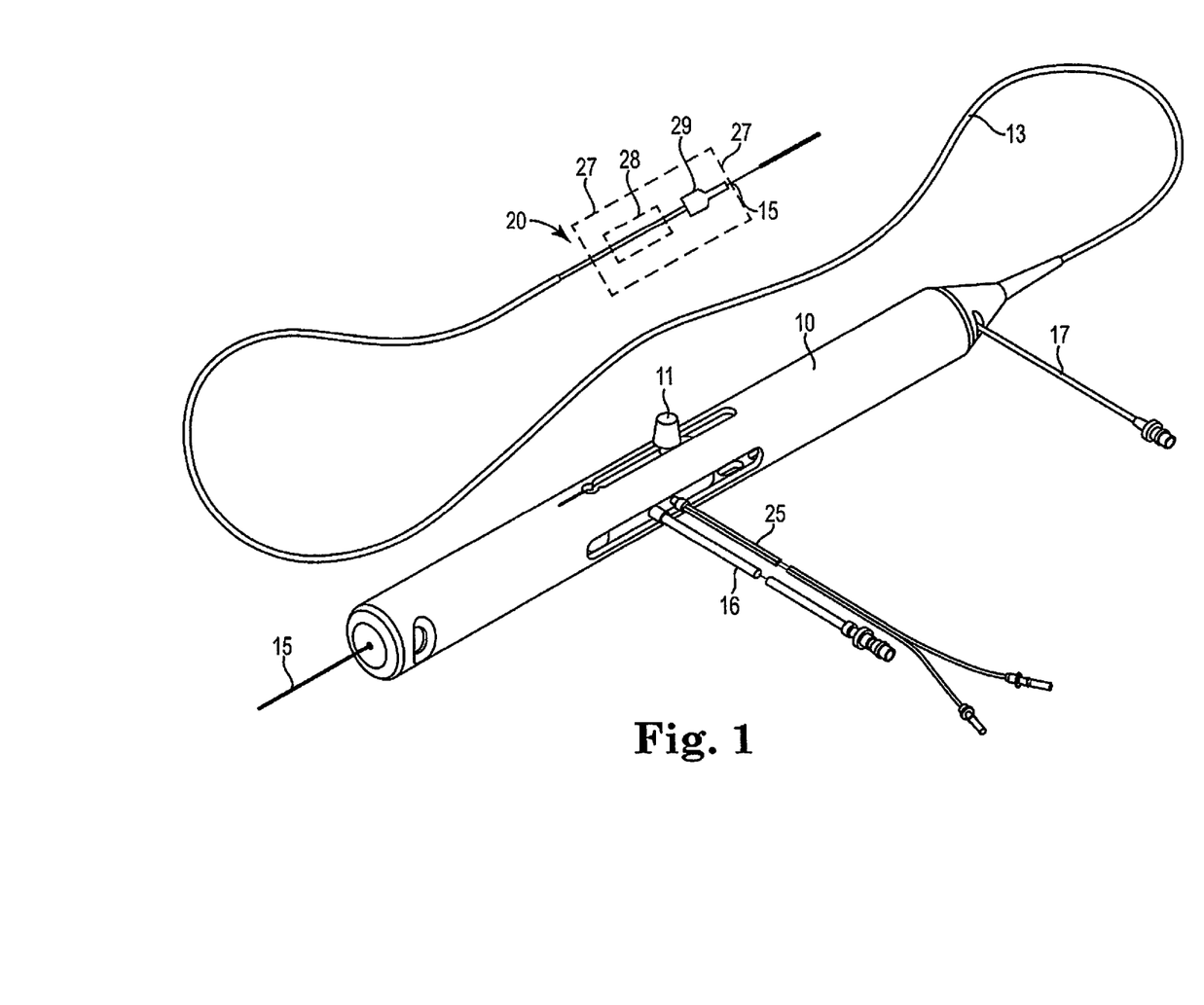
FIG. 1 is a perspective view of one embodiment of the present invention.

FIG. 1 illustrates one embodiment of a rotational atherectomy device according to the present invention. The device includes a handle portion 10, an elongated, flexible drive shaft 20 having a system of eccentric abrading heads 27 comprising, in the illustrated embodiment and without limitation, a proximal eccentric enlarged abrading head 28, a distal eccentric enlarged abrading head 29, and an elongated catheter 13 extending distally from the handle portion 10. The drive shaft 20 is constructed from helically coiled wire as is known in the art and the exemplary system 27 comprising the proximal abrading head 28 and distal abrading head 29 are fixedly attached thereto. The catheter 13 has a lumen in which most of the length of the drive shaft 20 is disposed, except for the enlarged proximal and distal abrading heads 28, 29 and a short section distal to the distal enlarged abrading head 29. The drive shaft 20 also contains an inner lumen, permitting the drive shaft 20 to be advanced and rotated over a guide wire 15. A fluid supply line 17 may be provided for introducing a cooling and lubricating solution (typically saline or another biocompatible fluid) into the catheter 13.

The handle 10 desirably contains a turbine (or similar rotational drive mechanism) for rotating the drive shaft 20 at high speeds. The handle 10 typically may be connected to a power source, such as compressed air delivered through a tube 16. A pair of fiber optic cables 25, alternatively a single fiber optic cable may be used, may also be provided for monitoring the speed of rotation of the turbine and drive shaft 20, details regarding such handles and associated instrumentation are well known in the industry. The handle 10 also desirably includes a control knob 11 for advancing and retracting the turbine and drive shaft 20 with respect to the catheter 13 and the body of the handle.

Proximal eccentric abrading head 28 and distal eccentric abrading head 29 of the illustrative system 27 are attached or otherwise disposed on or integrated with or formed from the drive shaft. Proximal abrading head 28 is located at a more proximal position in relation to the distal abrading head 29, i.e., the distal abrading head 29 is closest to the distal end of drive shaft 20. A distance or spacing separates the proximal and distal abrading heads 28, 29 from each other along drive shaft 20. Moreover, proximal and distal abrading heads 28, 29 each comprise a resting diameter D and D', respectively. The present invention requires that the resting diameter D of proximal abrading head 28 is larger than the resting diameter D' of distal abrading head 29. Further, the present invention is not limited to a system 27 comprising two abrading heads and, therefore, may comprise more than one abrading head. In all cases, however, the resting diameter of the most distal abrading head, e.g., 29, will be the smallest diameter abrading head, with each successively more proximal abrading head, e.g., 28, comprising a larger resting diameter than the adjacent distal head, e.g., 29. Stated differently, the abrading heads will increase in resting diameter moving from the distal end of the drive shaft 20 to a more proximal position on the drive shaft, with the most distal abrading head comprising the smallest resting diameter of all abrading heads.

The preferred embodiment comprises two abrading heads, i.e., 28, 29, as illustrated. An exemplary resting diameter D for the proximal abrading head may be in the range of 2 mm to 3 mm while the distal abrading head may comprise a resting diameter D' range of 1.25 to 5 mm. As discussed above, however, in each embodiment, the most distal abrading head has the smallest resting diameter in the system 27, with successively more proximal abrading head(s) comprising successively larger resting diameters.

Thus, one of the purposes of the primary invention is to provide a system of abrading heads 27 comprising a smaller resting diameter distal eccentric abrading head 29 in conjunction with at least one larger resting diameter proximal eccentric abrading head 28. The small diameter of the distal eccentric abrading head 29 may therefore be positioned within a small hole in the occlusive material in the patient's vasculature prior to high speed rotation therein. Initiation of rotation of the drive shaft 20 causes the system comprising drive shaft 20 with abrading heads 28, 29 mounted thereon, to begin to generate centrifugal forces as will be described in more detail herein. The result is, among other things, orbital motion of the abrading heads 28, 29, wherein the abrading heads 28, 29 begin to trace out paths that comprise working diameters that are, e.g., two to three times larger than the respective resting diameters D, D'.

Figure 2:
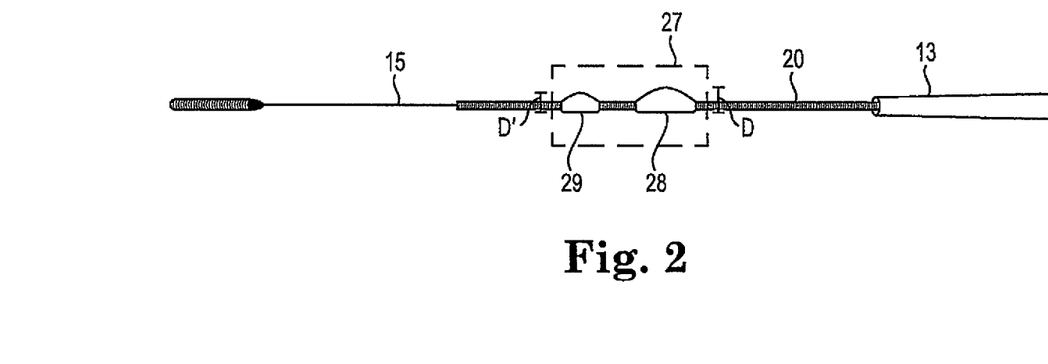
FIG. 2 is a side and partial cutaway view of one embodiment of the present invention.
Figure 3A:
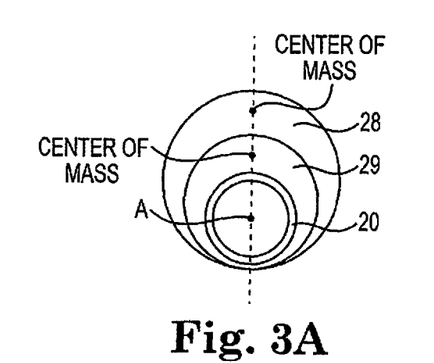
FIG. 3A is an end view of one embodiment of the present invention.

FIGS. 2, 3A and 3B provide illustration of the arrangement of certain embodiments of the system 27. Thus, FIGS. 2 and 3A illustrate an unbalanced system of abrading heads 27 comprising a proximal abrading head 28 and a distal abrading head 29 attached to the drive shaft 20, separated by a distance and wherein the centers of mass of both abrading heads 28, 29 are radially offset from the axis of rotation A of the drive shaft 20 in the same direction and in the same plane as illustrated by the dashed line in FIG. 3A. Stated differently, the offset of the center of mass of the entire system of abrading heads 27 is maximized in one radially offset direction, e.g., along the dashed line of FIG. 3A. A balanced embodiment would comprise, e.g., the centers of mass of the proximal abrading head 28 and the distal abrading head 29 to be separated rotationally by 180 degrees, whereby the centers of mass of the abrading heads 28, 29 would be on dashed line of FIG. 3A, but on opposing sides of the rotational axis of the drive shaft 20. Alternatively, an even number, e.g., four, of eccentric abrading heads could be provided, with rotational separation of equivalent rotational angle between each of the exemplary four eccentric abrading heads being equivalent, e.g., 45 degrees or 90 degrees or the like to achieve a balanced system. In this balanced embodiment, a preferred arrangement provides the centers of mass of the eccentric abrading heads being roughly equivalent in mass, though the resting diameters decrease successively moving from most proximal to most distal eccentric abrading head.

Figure 3B:
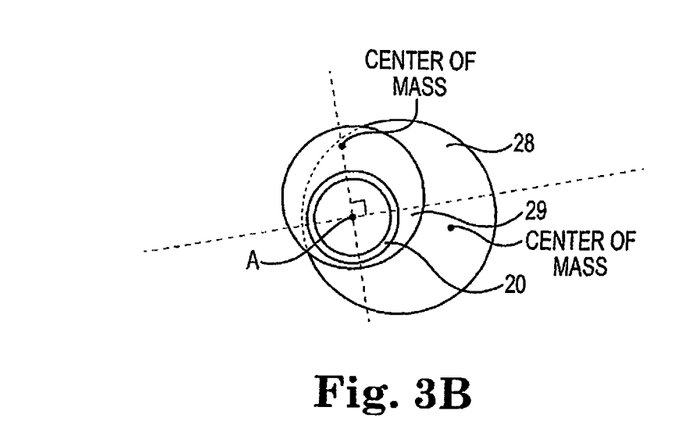
FIG. 3B is an end view of one embodiment of the present invention.

FIG. 3B illustrates an alternate embodiment of an unbalanced system of abrading heads 27. In this illustrative embodiment, the proximal and distal abrading heads 28, 29 are affixed or mounted on or formed from the drive shaft 20 and separated by a distance as in the embodiment of FIGS. 2 and 3A. However, the embodiment of 3B comprises the centers of mass of the proximal and distal abrading heads 28, 29 being radially offset from the axis of rotation of the drive shaft in different directions and different planes. Thus, as shown, the center of mass of distal abrading head 29 is substantially aligned with the rotational axis of the drive shaft 20 in a vertical direction, as illustrated by vertical dashed line. However, the center of mass of the proximal abrading head 28 is not on that vertical dashed line and is, in fact, provided in an approximately 100 degrees rotation from the vertical dashed line representing the plane comprising the center of mass of the distal abrading head 29. As a result, the system of abrading heads 27 comprises an unbalanced weight which, as with the system 27 of FIG. 3A, will tend to result in centrifugal forces generated during high speed rotation of the drive shaft 20 and orbital motion of the abrading heads 28, 29.

The primary difference between the embodiment of FIG. 3A and that of FIG. 3B comprises the influencing of fluid flow distally along the drive shaft 20 within the system of abrading heads 27 during high speed rotation and orbital motion of the heads 28, 29. FIG. 3A will generate a turbulence without a regular pattern of the surrounding fluid, comprising not only blood but also the debris abraded from the occlusion during high speed rotation.

FIG. 3B, in contrast, provides a generally spiral profile moving down the drive shaft 20 from a point proximal to the proximal abrading head 28 distally to a point distal to the distal abrading head 29. This spiraling profile is a result of the rotational spacing of the centers of mass of the abrading heads 28, 29, in the illustrated case approximately 100 degrees. In the illustrated case, the radial offset of the centers of mass is achieved by an eccentricity of the abrading heads 28, 29 provided by a geometric eccentricity. Stated differently, the geometric longitudinal profile of the abrading heads 28, 29 is eccentric. As a consequence, the profile of the system 27 comprises a spiral channel as described above along which fluid flow occurs. The result of this spiral profile during high speed rotation is that the fluid comprising blood and debris will tend to move along the spiral in a distal direction, from the larger diameter proximal abrading head 28 distally toward and beyond the smaller distal abrading head 29. Thus, the debris generated by the atherectomy procedure by system 27 is channeled away from the occlusion along the spiral channel of the system 27 in a controlled fashion.

Figure 4A:
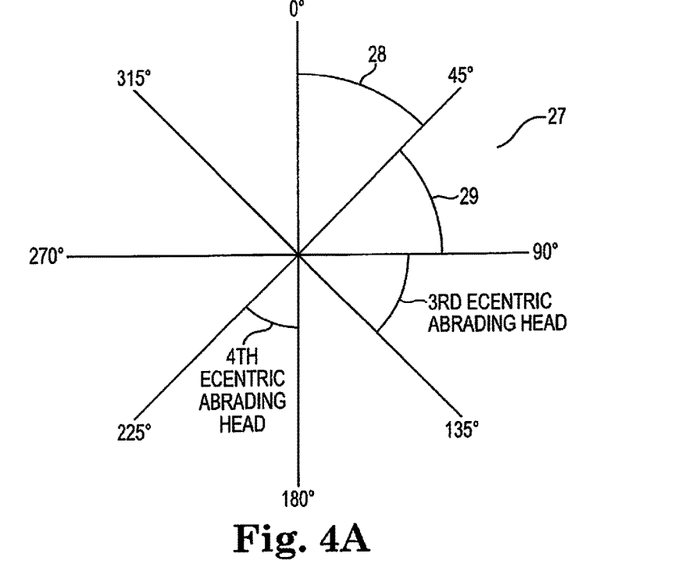
FIG. 4A is a schematic chart illustrating possible rotational angle separations of the present invention.

The spiral channel of system 27 is further illustrated in FIG. 4A which provides a longitudinal cross sectional view of drive shaft 20 with axis of rotation A with a rotational angle grid superimposed thereon. The rotational angle grid is broken into exemplary 45 degree sections around the drive shaft 20. Creation of the spiral channel and profile thereof may be achieved by rotationally separating the geometric centers, and centers of mass, of the eccentric abrading heads of the system 27. By way of example, an eccentric proximal abrading head 28 may comprise a geometric center, and a center of mass, located rotationally within the 0 degree to 45 degree rotational section as illustrated. A distal eccentric abrading head 29 may then be disposed so that its geometric center, and center of mass, is rotationally located within the rotational section comprising 45 degrees to 90 degrees. If, in certain embodiments, more than two abrading heads comprise the system 27, then, as illustrated, a third eccentric abrading head may be disposed with its geometric center and center of mass is rotationally located within the rotational section comprising 90 degrees to 135 degrees. If additional eccentric abrading heads, e.g., a fourth eccentric abrading head etc., are in system 27, their geometric centers and centers of mass will preferably be located in rotational sections greater than 135 degrees using the same logical progression.

The rotational sections illustrated are exemplary only and the skilled artisan will recognize that sections may be larger and/or smaller. Further, the skilled artisan will recognize that, e.g., proximal eccentric abrading head 28 may be separated more than 45 degrees from the distal eccentric abrading head 29.

Figure 4B:
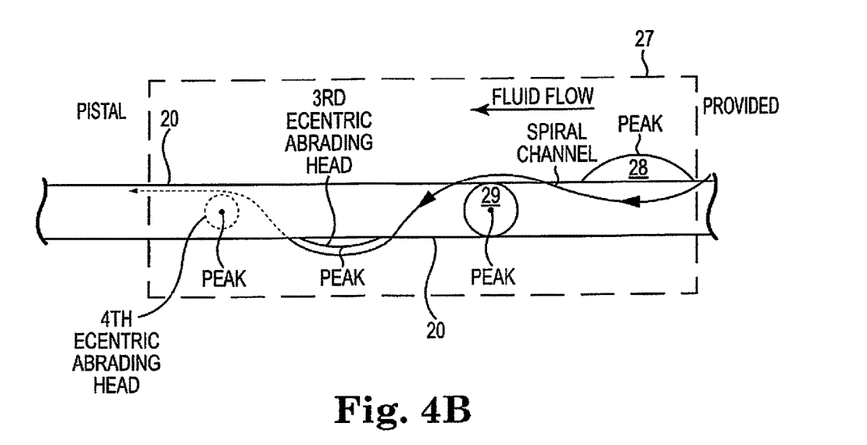
FIG. 4B is a side and cutaway view of one embodiment of the present invention.

The net effect of this rotational progression moving longitudinally along drive shaft 20 within system 27 is provision of a spiral channel as illustrated in FIG. 4B, with the fluid flow, including blood, cooling solution and debris, along the fluid flow line between the peaks of the successively mounted, and rotationally separated, abrading heads of system 27. The channeled spiraling of the fluid is enhanced and aided by the abrading head peaks engaging the occlusion.

The abrading heads of the system of abrading heads 27 may comprise one or more types of abrading heads.

Figure 5:
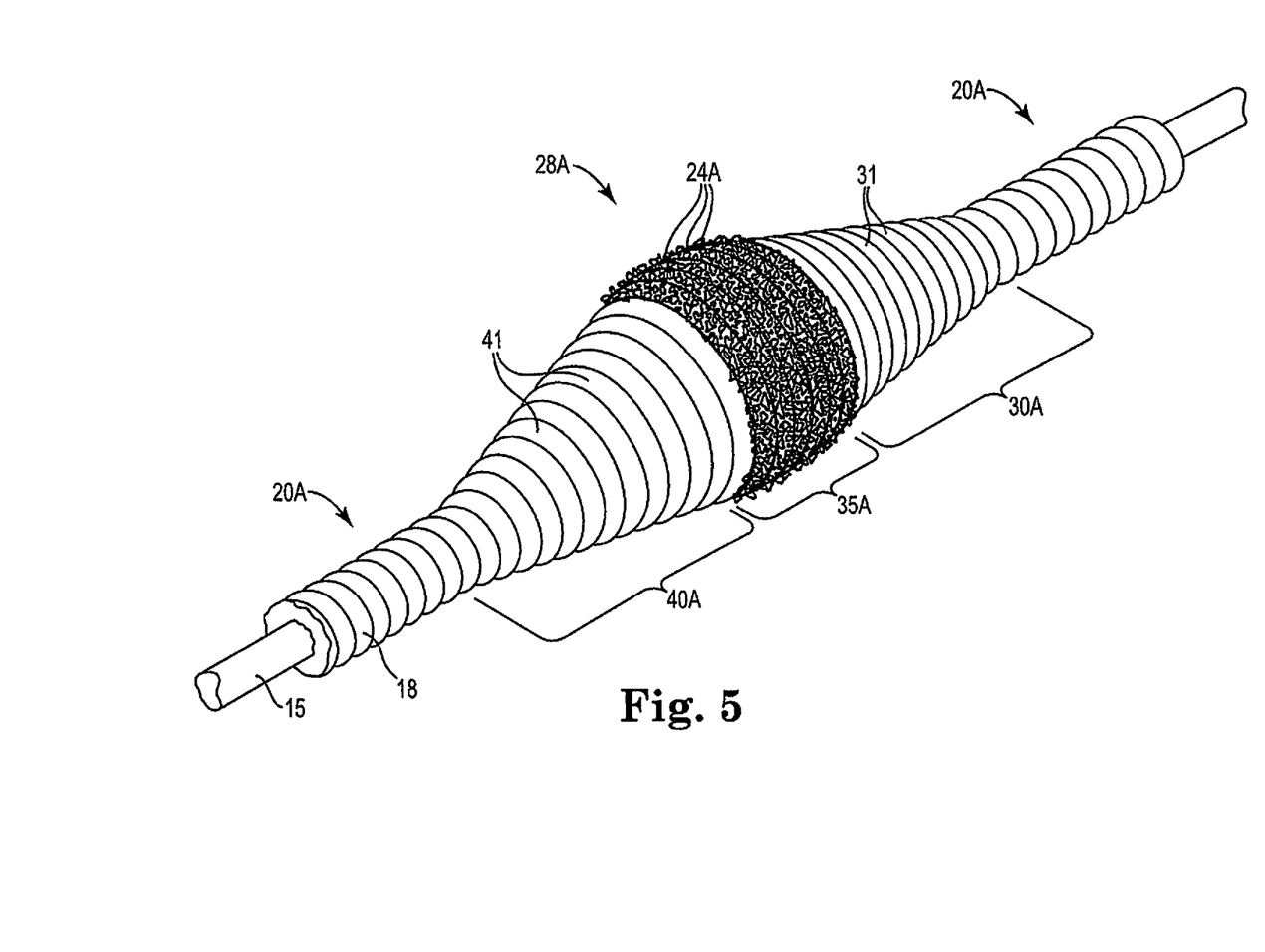
FIG. 5 is a perspective and cutaway view of one embodiment of the present invention.
Figure 6:
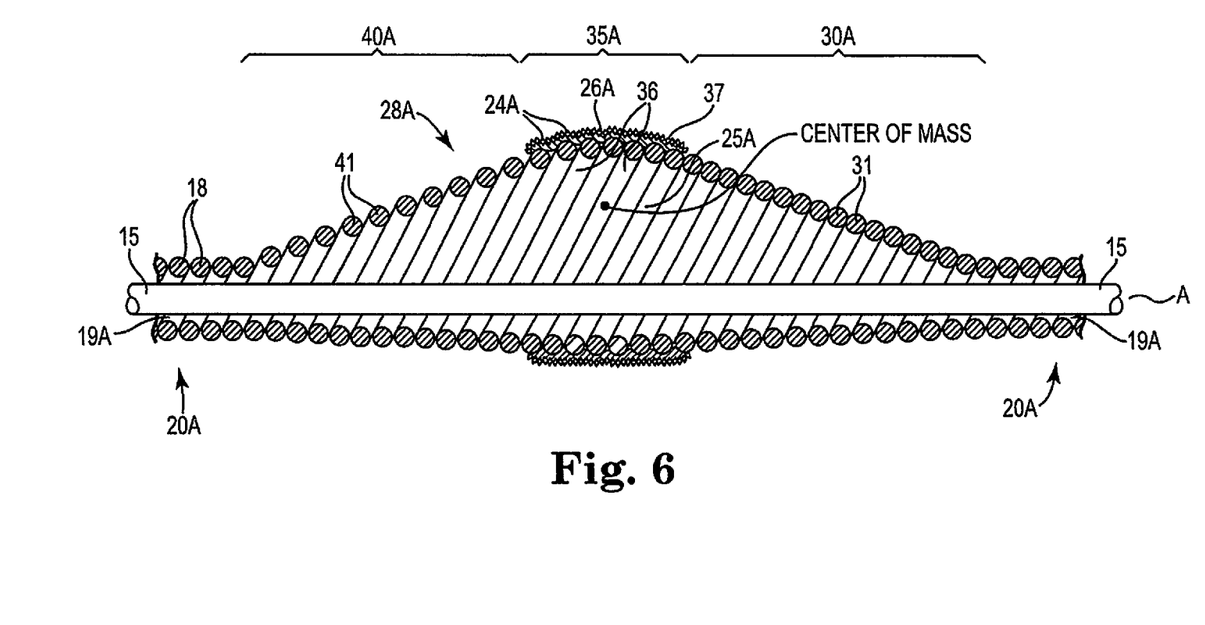
FIG. 6 is a side cutaway view of one embodiment of the present invention.

For example, FIGS. 5 and 6 illustrate an abrading head which may be used for one, or more, of the abrading heads, e.g., proximal and distal abrading heads 28, 29, of the present invention. This embodiment comprises an eccentric enlarged diameter abrading section 28A of a drive shaft 20A. Note that this embodiment is designated as 28A for instructive purposes only, this designation does not limit the illustrated embodiment to a proximal abrading head position on the drive shaft. The drive shaft 20A comprises one or more helically wound wires 18 which define a guide wire lumen 19A and a hollow cavity 25A within the enlarged abrading section 28A. Except for the guide wire 15 traversing the hollow cavity 25A, the hollow cavity 25A is substantially empty. The eccentric enlarged diameter abrading section 28A includes, relative to the location of the stenosis, proximal 30A, intermediate 35A and distal 40A portions. Wire turns 31 of the proximal portion 30A of the eccentric enlarged diameter section 28A preferably have diameters that progressively increase distally at a generally constant rate, thereby forming generally the shape of a cone. Wire turns 41 of the distal portion 40A preferably have diameters that progressively decrease distally at a generally constant rate, thereby forming generally the shape of a cone. Wire turns 36 of the intermediate portion 35A are provided with gradually changing diameters to provide a generally convex outer surface which is shaped to provide a smooth transition between the proximal and distal conical portions of the enlarged eccentric diameter section 28A of the drive shaft 20A. In this abrading head embodiment, the center of mass is located radially offset from the drive shaft axis of rotation A.

Further, at least part of the eccentric enlarged diameter abrading section of the drive shaft 28A (preferably the intermediate portion 35A) comprises an external surface capable of removing tissue. A tissue removing surface 37 comprising a coating of an abrasive material 24A to define a tissue removing segment of the drive shaft 20A is shown attached directly to the wire turns of the drive shaft 20A by a suitable binder 26A.

FIGS. 5 and 6 thus illustrate one embodiment of the enlarged diameter abrading section disclosed in commonly assigned U.S. Pat. No. 6,494,890 (Shturman) wherein at least a segment of this enlarged section is covered with an abrasive material and which may be used in present invention's system 27. When rotated at high speeds, the abrasive segment is capable of removing stenotic tissue from an artery. The device is capable of opening an artery to a diameter that is larger than the resting diameter of the enlarged eccentric section due, in part, to the orbital rotational motion during high speed operation. Since the enlarged eccentric section comprises drive shaft wires that are not bound together, the enlarged eccentric section of the drive shaft may flex during placement within the stenosis or during high speed operation. This flexion allows for a larger diameter opening during high speed operation. The disclosure of U.S. Pat. No. 6,494,890 is hereby incorporated by reference in its entirety.

Turning now to FIGS. 7 and 8A-8C, another embodiment of a possible abrading head comprising system of eccentric abrading heads 27 of the present invention will be discussed. As with the embodiment of FIGS. 4 and 5, the instant embodiment may be used for one, or more, of the abrading heads of the system of eccentric abrading heads 27. By way of non-limiting example, the instant embodiment may comprise one or both of the proximal and/or distal abrading heads 28, 29. Alternatively, the instant embodiment may be combined with another type of abrading head, e.g., that embodiment illustrated in FIGS. 5 and 6 to comprise system 27. Thus, the instant embodiment may comprise the proximal abrading head 28 and the embodiment of FIGS. 5 and 6 may comprise the distal abrading head 29 to form system 27. Many other equivalent variations and combinations present themselves readily to the skilled artisan, each such combination is within the scope of the present invention.

As discussed above, the drive shaft 20 has a rotational axis A which is coaxial with the guide wire 15, the guide wire 15 being disposed within the lumen 19 of the drive shaft 20. With particular reference to FIGS. 7 and 8A-8C, the proximal portion 30S of the eccentric enlarged abrading head 28S has an outer surface which is substantially defined by the lateral surface of a frustum of a cone, the cone having an axis 32 which intersects the rotational axis 21 of the drive shaft 20 at a relatively shallow angle β. Similarly, the distal portion 40S of the enlarged abrading head 28S has an outer surface which is substantially defined by the lateral surface of a frustum of a cone, the cone having an axis 42 which also intersects the rotational axis 21 of the drive shaft 20 at a relatively shallow angle β. The cone axis 32 of the proximal portion 30S and the cone axis 42 of the distal portion 40S intersect each other and are coplanar with the longitudinal rotational axis A of the drive shaft.

The opposing sides of the cones generally should be at an angle α of between about 10° and about 30° with respect to each other; preferably the angle α is between about 20° and about 24°, and most preferably the angle α is about 22°. Also, the cone axis 32 of the proximal portion 30S and the cone axis 42 of the distal portion 40S normally intersect the rotational axis 21 of the drive shaft 20 at an angle β of between about 20° and about 8°. Preferably the angle β is between about 3° and about 6°. Although in the preferred embodiment shown in the drawings the angles α of the distal and proximal portions of the enlarged abrading head 28S are generally equal, they need not be equal. The same is true for the angles β.

Figure 7:
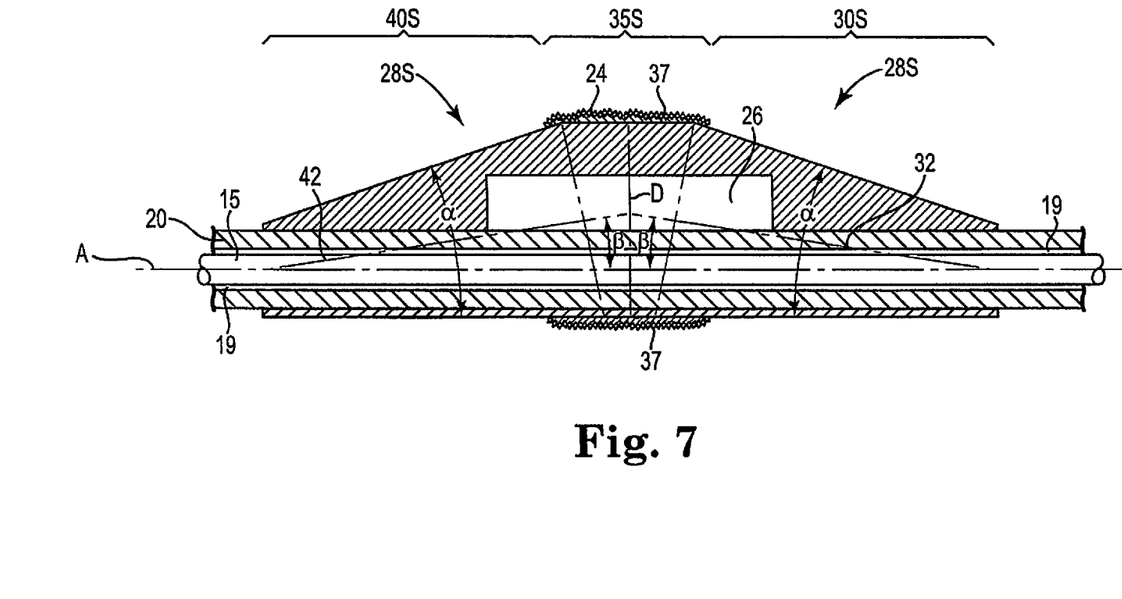
FIG. 7 is a side cutaway view of one embodiment of the present invention.

In an alternate embodiment, the intermediate portion 35S may comprise a diameter that gradually increases from the intersection with the distal portion 40 to the intersection of the proximal portion 30. In this embodiment, angle α, as illustrated in FIG. 7, may be larger in the proximal portion 30S than the distal portion 40S, or vice versa. Further alternate embodiments comprise the intermediate portion 35S having a surface that is convex, wherein the intermediate portion outer surface may be shaped to provide a smooth transition between the proximal and distal outer surfaces of the proximal and distal portions.

The abrading head 28S may comprise at least one tissue removing surface 37 on the external surface(s) of the intermediate portion 35S, the distal portion 40S and/or the proximal portion 30S to facilitate abrasion of the stenosis during high speed rotation. The tissue removing surface 37 may comprise a coating of an abrasive material 24 bound to the external surface(s) of the intermediate portion 35S, the distal portion 40S and/or the proximal portion 30S of abrading head 28S. The abrasive material may be any suitable material, such as diamond powder, fused silica, titanium nitride, tungsten carbide, aluminum oxide, boron carbide, or other ceramic materials. Preferably the abrasive material is comprised of diamond chips (or diamond dust particles) attached directly to the tissue removing surface(s) by a suitable binder—such attachment may be achieved using well known techniques, such as conventional electroplating or fusion technologies (see, e.g., U.S. Pat. No. 4,018,576). Alternately the external tissue removing surface may comprise mechanically or chemically roughening the external surface(s) of the intermediate portion 35S, the distal portion 40S and/or the proximal portion 30S to provide a suitable abrasive tissue removing surface 37. In yet another variation, the external surface may be etched or cut (e.g., with a laser) to provide small but effective abrading surfaces. Other similar techniques may also be utilized to provide a suitable tissue removing surface 37.

Figure 8A:
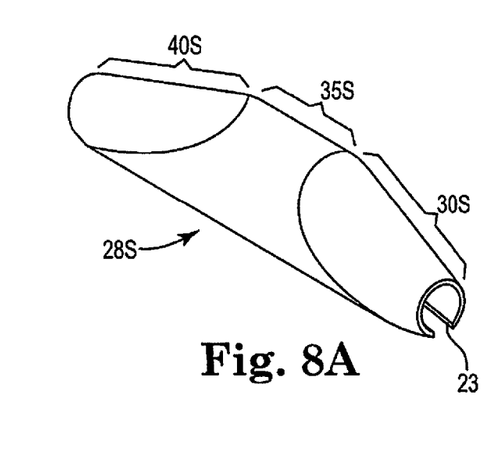
FIG. 8A is a perspective view of one embodiment of the present invention.
Figure 8B:
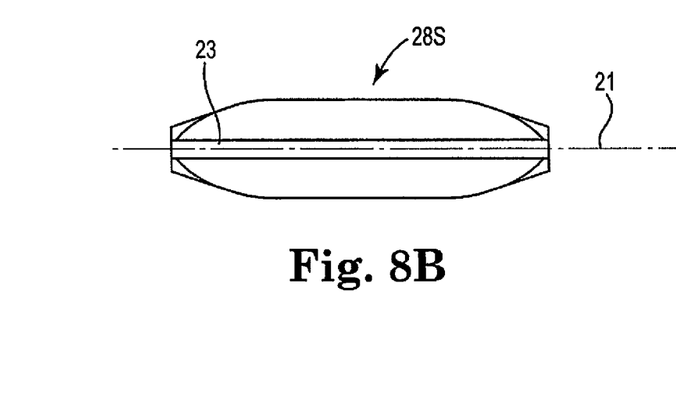
FIG. 8B is a bottom view of one embodiment of the present invention.
Figure 8C:
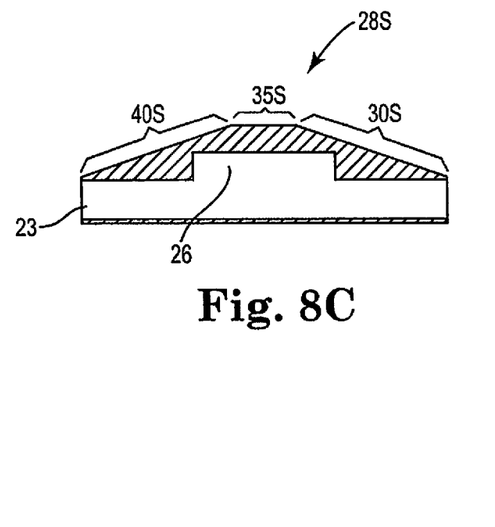
FIG. 8C is a side cutaway view of one embodiment of the present invention.

As best illustrated in FIGS. 8A-8C, an at least partially enclosed lumen or slot 23 may be provided longitudinally through the enlarged abrading head 28S along the rotational axis 21 of the drive shaft 20 for securing the abrading head 28 to the drive shaft 20 in a manner well known to those skilled in the art. In the embodiment shown, a hollowed section 26 is provided to lessen the mass of the abrading head 28S to facilitate atraumatic abrasion and improve predictability of control of the orbital pathway of the abrading head 28S during high speed, i.e., 20,000 to 200,000 rpm, operation. In this embodiment, the abrading head 28S may be fixedly attached to the drive shaft 20, wherein the drive shaft comprises one single unit. Alternatively, the drive shaft 20 may comprise two separate pieces, wherein the enlarged eccentric abrading head 28S is fixedly attached to both drive shaft 20 pieces, with a gap therebetween. This two-piece drive shaft construction technique may, in combination with hollowed section 26, allow further manipulation of the placement of the center of mass of the abrading head 28S. The size and shape of the hollowed section 26 in all embodiments may be modified to optimize the orbital rotational path of the abrading head 28S for particularly desirable rotational speeds. It is understood that hollow section 26 is illustrated as symmetrical in all planes, though this is certainly not a limiting example. Hollowed section 26 may be asymmetric longitudinally and/or radially in order to move the center of mass of the abrading head 28S to the desired location. Those skilled in the art will readily recognize the various possible configurations, each of which is within the scope of the present invention.

Further, the embodiment of FIGS. 7, 8A-8C illustrates the proximal portion 30S and distal portion 40S of symmetrical shape and length. Alternate embodiments may increase the length of either the proximal portion 30S or the distal portion 40S, to create an asymmetrical profile.

Because the cone axes 32 and 42 intersect the rotational axis 21 of the drive shaft 20 at an angle β the eccentric enlarged abrading head 28S has a center of mass that is spaced radially away from the longitudinal rotational axis 21 of the drive shaft 20. As will be described in greater detail below, offsetting the center of mass from the drive shaft's axis of rotation 21 provides the enlarged abrading head 28S with an eccentricity that permits it to open an artery to a diameter substantially larger, than the nominal diameter of the enlarged eccentric abrading head 28S, preferably the opened diameter is at least twice as large as the nominal resting diameter of the enlarged eccentric abrading head 28S.

It is understood that, as used herein, the word "eccentric" is defined and used herein to refer to either a difference in location between the geometric center of the enlarged abrading head 28S and the rotational axis 21 of the drive shaft 20, or to a difference in location between the center of mass of system 27 components exemplary enlarged abrading head 28S and/or eccentric abrading head 28A and the rotational axis 21 of the drive shaft 20. Either such difference, at the proper rotational speeds, will enable the system 27 components eccentric enlarged abrading head 28S, 28A to open a stenosis to a diameter substantially greater than the nominal diameter of the eccentric enlarged abrading head 28S, 28A. Moreover, for an eccentric enlarged abrading head 28S, 28A having a shape that is not a regular geometric shape, the concept of "geometric center" can be approximated by locating the mid-point of the longest chord which is drawn through the rotational axis 21 of the drive shaft 28 and connects two points on a perimeter of a transverse cross-section taken at a position where the perimeter of the eccentric enlarged abrading head 28S, 28A has its maximum length.

The abrading head 28S and/or 28A of the rotational atherectomy device of the invention may be constructed of stainless steel, tungsten or similar material. The abrading head 28 may be a single piece unitary construction or, alternatively, may be an assembly of two or more abrading head components fitted and fixed together to achieve the objects of the present invention.

The extent to which a stenosis in an artery can be opened to a diameter larger than the nominal diameter of the eccentric enlarged abrading head of the present invention depends on several parameters, including the shape of the eccentric enlarged abrading head, the mass of the eccentric enlarged abrading head, the distribution of that mass and, therefore, the location of the center of mass within the abrading head with respect to the rotational axis of the drive shaft, and the speed of rotation.

The speed of rotation is a significant factor in determining the centrifugal force with which the tissue removing surface of the enlarged abrading head is pressed against the stenotic tissue, thereby permitting the operator to control the rate of tissue removal. Control of the rotational speed also allows, to some extent, control over the maximum diameter to which the device will open a stenosis. Applicants have also found that the ability to reliably control the force with which the tissue removing surface is pressed against the stenotic tissue not only permits the operator to better control the rate of tissue removal but also provides better control of the size of the particles being removed.

Figure 9:
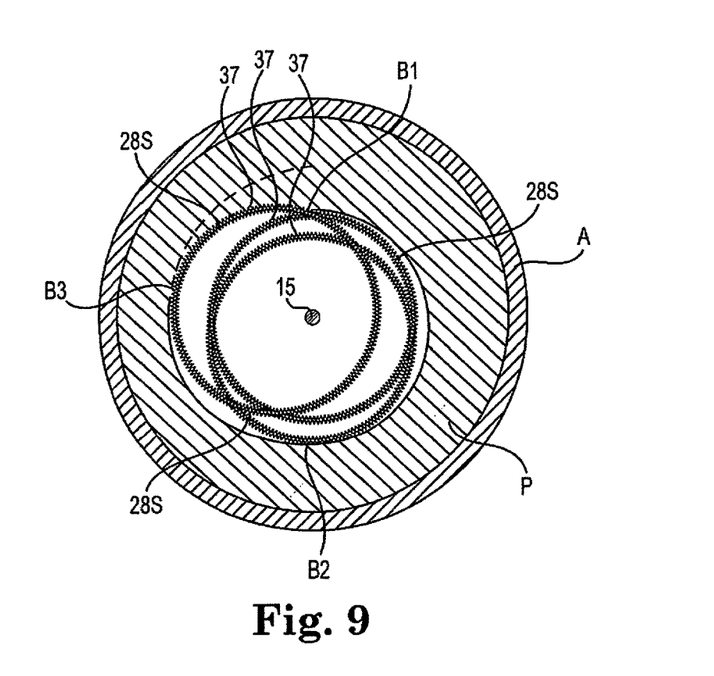
FIG. 9 is a cutaway view of one embodiment of the present invention.
Figure 10:
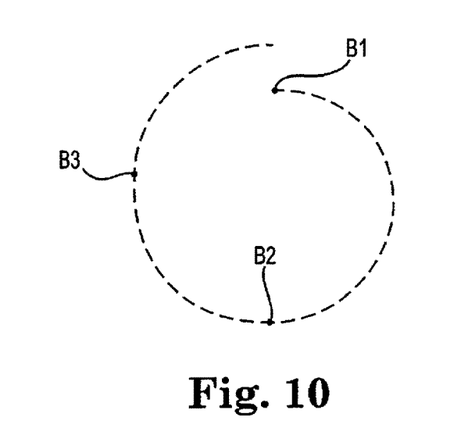
FIG. 10 is a schematic view illustrating of one embodiment of the present invention.

FIG. 9 illustrates the generally spiral orbital path taken by various embodiments of an exemplary system 27 eccentric abrading heads comprising 28S and/or 28A of the present invention, the abrading head 28 shown relative to the guide wire 15 over which the abrading head 28A and/or 28S has been advanced. The pitch of the spiral path in FIG. 9 is exaggerated for illustrative purposes—in reality, each spiral path of the system 27 comprising eccentric enlarged abrading heads 28A and/or 28S removes only a very thin layer of tissue via the tissue removing surface 37, and many, many such spiral passes are made by the system 27 as the device is repeatedly moved forward and backward across the stenosis to fully open the stenosis. FIG. 10 shows schematically three different rotational positions of the eccentric enlarged abrading head 28S and/or 28A of a rotational atherectomy device of the invention. At each position the abrasive surface of the eccentric enlarged abrading head 28S and/or 28A contacts the plaque "P" to be removed—the three positions are identified by three different points of contact with the plaque "P", those points being designated in the drawing as points B1, B2, and B3. Notice that at each point it is generally the same portion of the abrasive surface of the eccentric enlarged abrading head 28S and/or 28A that contacts the tissue—the portion of the tissue removing surface 37 that is radially most distant from the rotational axis of the drive shaft.

Although not wishing to be constrained to any particular theory of operation, applicants believe that offsetting the center of mass from the axis of rotation produces an "orbital" movement of the enlarged abrading head, the diameter of the "orbit" being controllable by varying, inter alis, the rotational speed of the drive shaft. Applicants have empirically demonstrated that by varying the rotational speed of the drive shaft one can control the centrifugal force urging the tissue removing surface of the eccentric enlarged abrading head 28S and/or 28A against the surface of the stenosis. The centrifugal force can be determined according to the formula:

$$F_c = m \, \Delta x (\pi n/30)^2$$

where $F_c$ is the centrifugal force, m is the mass of the eccentric enlarged abrading head, Δx is the distance between the center of mass of the eccentric enlarged abrading head and the rotational axis of the drive shaft, and n is the rotational speed in revolutions per minute (rpm). Controlling this force $F_c$ provides control over the rapidity with which tissue is removed, control over the maximum diameter to which the device will open a stenosis, and improved control over the particle size of the tissue being removed.

The abrading head 28S and/or 28A of the present invention comprises more mass than prior art high speed atherectomy abrading devices. As a result, a larger orbit may be achieved during high speed rotation which, in turn, allows for use of a smaller abrading head than with prior art devices. In addition to allowing for the creation of pilot holes in completely or substantially blocked arteries and the like, using a smaller abrading head will allow for greater ease of access and less trauma during insertion.

Operationally, using the rotational atherectomy device of the invention the eccentric enlarged abrading head 28S and/or 28A is repeatedly moved distally and proximally through the stenosis. By changing the rotational speed of the device he or she is able to control the force with which the tissue removal surface is pressed against the stenotic tissue, thereby being able to better control the speed of the plaque removal as well as the particle size of tissue removed. In addition, the successively increasing (from distal to proximal) resting diameters of the more than one eccentric abrading heads of the system 27 enables opening the stenosis to a diameter larger than the resting diameter of the enlarged eccentric abrading head, e.g., 28S and/or 28A. In addition, in the unbalanced embodiment described above wherein a spiral channel is formed around the eccentric abrading heads of system 27, the cooling solution and blood are able to constantly flow around the enlarged abrading heads. Such constant flow of blood and cooling solution constantly flushes away removed tissue particles down the spiral channel, thus providing uniform release of removed particles, once the abrading head has passed through the lesion once.

The eccentric enlarged abrading head 28S and/or 28A may comprise a maximum cross-sectional diameter ranging between about 1.0 mm to about 3.0 mm. Thus, the eccentric enlarged abrading head may comprise cross-sectional diameters including, but not limited to: 1.0 mm, 1.25 mm, 1.50 mm, 1.75 mm, 2.0 mm, 2.25 mm, 2.50 mm, 2.75 mm, and 3.0 mm. Those skilled in the art will readily recognize that the incremental increases of 0.25 mm within the above-listing of cross-sectional diameter are exemplary only, the present invention is not limited by the exemplary listing and, as a result, other incremental increases in cross-sectional diameter are possible and within the scope of the present invention.

Because, as described above, the eccentricity of the enlarged abrading head 28S and/or 28A is dependent on a number of parameters, applicants have found that the following design parameters may be considered regarding the distance between the rotational axis 21 of the drive shaft 20 and the geometric center of a face of a transverse cross-section, taken at a position of maximum cross-sectional diameter of the eccentric enlarged abrading head: for a device having an eccentric enlarged abrading head with a maximum cross-sectional diameter between about 1.0 mm and about 1.5 mm, desirably the geometric center should be spaced away from the rotational axis of the drive shaft by a distance of at least about 0.02 mm, and preferably by a distance of at least about 0.035 mm; for a device having an eccentric enlarged abrading head with a maximum cross-sectional diameter between about 1.5 mm and about 1.75 mm, desirably the geometric center should be spaced away from the rotational axis of the drive shaft by a distance of at least about 0.05 mm, preferably by a distance of at least about 0.07 mm, and most preferably by a distance of at least about 0.09 mm; for a device having an eccentric enlarged abrading head with a maximum cross-sectional diameter between about 1.75 mm and about 2.0 mm, desirably the geometric center should be spaced away from the rotational axis of the drive shaft by a distance of at least about 0.1 mm, preferably by a distance of at least about 0.15 mm, and most preferably by a distance of at least about 0.2 mm; and for a device having an eccentric enlarged abrading head with a maximum cross-sectional diameter above 2.0 mm, desirably the geometric center should be spaced away from the rotational axis of the drive shaft by a distance of at least about 0.15 mm, preferably by a distance of at least about 0.25 mm, and most preferably by a distance of at least about 0.3 mm.

Design parameters can also be based on the location of the center of mass. For a device having an eccentric enlarged abrading head 28S and/or 28A with a maximum cross-sectional diameter between about 1.0 mm and about 1.5 mm, desirably the center of mass should be spaced away from the rotational axis of the drive shaft by a distance of at least about 0.013 mm, and preferably by a distance of at least about 0.02 mm; for a device having an eccentric enlarged abrading head 28S and/or 28A with a maximum cross-sectional diameter between about 1.5 mm and about 1.75 mm, desirably the center of mass should be spaced away from the rotational axis of the drive shaft by a distance of at least about 0.03 mm, and preferably by a distance of at least about 0.05 mm; for a device having an eccentric enlarged abrading head with a maximum cross-sectional diameter between about 1.75 mm and about 2.0 mm, desirably the center of mass should be spaced away from the rotational axis of the drive shaft by a distance of at least about 0.06 mm, and preferably by a distance of at least about 0.1 mm; and for a device having an eccentric enlarged abrading head with a maximum cross-sectional diameter above 2.0 mm, desirably the center of mass should be spaced away from the rotational axis of the drive shaft by a distance of at least about 0.1 mm, and preferably by a distance of at least about 0.16 mm.

The present invention should not be considered limited to the particular examples described above, but rather should be understood to cover all aspects of the invention. Various modifications, equivalent processes, as well as numerous structures to which the present invention may be applicable will be readily apparent to those of skill in the art to which the present invention is directed upon review of the present specification.

What is claimed is:

1. A high-speed rotational atherectomy device for opening a stenosis in an artery having a given diameter, comprising:
   a guide wire having a maximum diameter less than the diameter of the artery;
   a flexible elongated, rotatable drive shaft advanceable over the guide wire, the drive shaft having a rotational axis; and
   an unbalanced system of more than one eccentric abrading head in spaced apart longitudinal disposition along the drive shaft, the more than one eccentric abrading heads each having a resting diameter, wherein a distal eccentric abrading head comprises a resting diameter that is the smallest resting diameter in the unbalanced system and the remaining eccentric abrading heads in the unbalanced system comprise resting diameters that increase successively from distal to proximal, wherein the most proximal eccentric abrading head comprises the largest resting diameter in the unbalanced system, each eccentric abrading head in the unbalanced system further comprising a geometric center and a center of mass, wherein the geometric center and center of mass are radially offset from the rotational axis of the drive shaft; and a spiral channel disposed between the successively spaced apart eccentric abrading heads defined by a rotational separation between adjacent eccentric abrading heads in the unbalanced system.

2. The rotational atherectomy device of claim 1, further comprising at least one of the more than one eccentric abrading heads comprising proximal, intermediate and distal portions, wherein the proximal portion comprises a proximal outer surface, the intermediate portion comprises an intermediate outer surface and the distal portion comprises a distal outer surface, the proximal outer surface having diameters that increase distally, the distal outer surface having diameters that decrease distally, and the intermediate outer surface being cylindrical, wherein at least the intermediate outer surface comprise tissue removal sections and wherein the at least one of the more than one eccentric abrading heads defines a drive shaft lumen therethrough and a hollow cavity, the drive shaft at least partially traversing the drive shaft lumen.

3. The rotational atherectomy device of claim 1, further comprising at least one of the eccentric abrading heads comprising an enlarged section of the drive shaft.

4. The rotational atherectomy device of claim 3, further comprising at least one of the more than one eccentric abrading heads comprising proximal, intermediate and distal portions, wherein the proximal portion comprises a proximal outer surface, the intermediate portion comprises an intermediate outer surface and the distal portion comprises a distal outer surface, the proximal outer surface having diameters that increase distally, the distal outer surface having diameters that decrease distally, and the intermediate outer surface being cylindrical, wherein at least the intermediate outer surface comprise tissue removal sections and wherein each of the at least one of the more than one eccentric abrading heads defines a drive shaft lumen therethrough and a hollow cavity, the drive shaft at least partially traversing the drive shaft lumen.

5. The rotational atherectomy device of claim 4, wherein the proximal outer surface of the at least one eccentric abrading head is substantially defined by a lateral surface of a cone, the cone having an axis that intersects the rotational axis of the drive shaft.

6. The rotational atherectomy device of claim 5, wherein the distal outer surface of the at least one eccentric abrading head is substantially defined by a lateral surface of a cone, the cone having an axis that intersects the rotational axis of the drive shaft.

7. The rotational atherectomy device of claim 1, wherein each of the more than one eccentric abrading heads defines a drive shaft lumen therethrough and wherein the portion of the drive shaft traversing the drive shaft lumen and attaching thereto comprises a single, unbroken drive shaft.

8. The rotational atherectomy device of claim 1, wherein the each of the more than one eccentric abrading heads defines a drive shaft lumen therethrough and wherein the portion of the drive shaft traversing the drive shaft lumen and attaching thereto comprises at least two sections, each section attached to the drive shaft lumen with a gap between the at least two drive shaft sections.

9. The device of claim 1, wherein the rotational separation between adjacent eccentric abrading heads is between 0 degrees and 45 degrees.

10. The device of claim 1, wherein the rotational separation between adjacent eccentric abrading heads is between 0 degrees and 90 degrees.

11. The device of claim 1, wherein the unbalanced system of at least one eccentric abrading head comprises a proximal eccentric abrading head and a distal eccentric abrading head and wherein the rotational separation between the proximal and distal eccentric abrading heads is about 45 degrees.

12. The device of claim 11, wherein the unbalanced system of at least one eccentric abrading head comprises a third eccentric abrading head in spaced apart longitudinal disposition between the proximal and the distal eccentric abrading heads, the distal eccentric abrading head having a resting diameter, the third eccentric abrading head having a resting diameter that is larger than the resting diameter of the distal eccentric abrading head, the proximal eccentric abrading having a resting diameter that is larger than the resting diameter of the third eccentric abrading head, wherein the rotational separation between the proximal and third eccentric abrading head is about 45 degrees and the rotational separation between the third eccentric abrading and the distal eccentric abrading head is about 45 degrees.

13. The device of claim 1, wherein the balanced system of at least one eccentric abrading head comprises an even number of eccentric abrading heads and wherein the rotational separation between each adjacent eccentric abrading heads in the balanced system is the same and between 0 degrees and 90 degrees.

14. The device of claim 13, wherein the rotational separation between adjacent eccentric abrading heads is the same and between 0 degrees and 45 degrees.

15. A high-speed rotational atherectomy device for opening a stenosis in an artery having a given diameter, comprising:
   a guide wire having a maximum diameter less than the diameter of the artery;
   a flexible elongated, rotatable drive shaft advanceable over the guide wire, the drive shaft having a rotational axis; and
   an balanced system of more than one eccentric abrading head in spaced apart longitudinal disposition along the drive shaft and comprising a distal eccentric abrading head and a proximal eccentric abrading head, the more than one eccentric abrading heads each having a resting diameter, wherein the distal eccentric abrading head comprises a resting diameter that is the smallest resting diameter in the unbalanced system and the remaining eccentric abrading heads in the balanced system comprise resting diameters that increase successively, wherein the proximal eccentric abrading head comprises a resting diameter that is the largest resting diameter in the balanced system, each eccentric abrading head in the balanced system further comprising a geometric center and a center of mass, wherein the geometric center and center of mass are radially offset from the rotational axis of the drive shaft; and
   a spiral channel disposed between the successively spaced apart eccentric abrading heads defined by a rotational separation between adjacent eccentric abrading heads in the balanced system.

16. The rotational atherectomy device of claim 15, further comprising at least one of the more than one eccentric abrading heads comprising proximal, intermediate and distal portions, wherein the proximal portion comprises a proximal outer surface, the intermediate portion comprises an intermediate outer surface and the distal portion comprises a distal outer surface, the proximal outer surface having diameters that increase distally, the distal outer surface having diameters that decrease distally, and the intermediate outer surface being cylindrical, wherein at least the intermediate outer surface comprise tissue removal sections and wherein the abrading head defines a drive shaft lumen therethrough and a hollow cavity, the drive shaft at least partially traversing the drive shaft lumen.

17. The rotational atherectomy device of claim 15, further comprising at least one of the eccentric abrading heads comprising an enlarged section of the drive shaft.

18. The rotational atherectomy device of claim 17, further comprising least one of the more than one eccentric abrading heads comprising proximal, intermediate and distal portions, wherein the proximal portion comprises a proximal outer surface, the intermediate portion comprises an intermediate outer surface and the distal portion comprises a distal outer surface, the proximal outer surface having diameters that increase distally, the distal outer surface having diameters that decrease distally, and the intermediate outer surface being cylindrical, wherein at least the intermediate outer surface comprise tissue removal sections and wherein the abrading head defines a drive shaft lumen therethrough and a hollow cavity, the drive shaft at least partially traversing the drive shaft lumen.

19. The rotational atherectomy device of claim 15, wherein each of the more than one eccentric abrading heads comprises a drive shaft lumen therethrough, the portion of the drive shaft traversing the drive shaft lumen and attaching thereto comprises a single, unbroken drive shaft.

20. A high-speed rotational atherectomy device for opening a stenosis in an artery having a given diameter, comprising:
  a guide wire having a maximum diameter less than the diameter of the artery;
  a flexible elongated, rotatable drive shaft advanceable over the guide wire, the drive shaft having a rotational axis; and
  an unbalanced system of more than one eccentric abrading head in spaced apart longitudinal disposition along the drive shaft, the more than one eccentric abrading heads each having a resting diameter, wherein each eccentric abrading head in the unbalanced system comprises a geometric center and a center of mass, wherein the geometric center and center of mass are radially offset from the rotational axis of the drive shaft and wherein the centers of mass are all offset radially in different directions and in different planes.

* * * * *